United States Patent [19]

Moore

[11] Plant 4,618

[45] Jan. 13, 1981

[54] ROSE PLANT

[76] Inventor: Ralph S. Moore, 2519 E. Noble Ave., Visalia, Calif. 93277

[21] Appl. No.: 72,558

[22] Filed: Sep. 4, 1979

[51] Int. Cl.[3] ..... A01H 5/00

[52] U.S. Cl. ..... Plt./8

[58] Field of Search ..... Plt./8

*Primary Examiner*—Robert E. Bagwill
*Assistant Examiner*—James R. Feyrer

[57] ABSTRACT

This invention relates to a new and distinct variety of miniature rose plant primarily identified by its white to near white buds and flowers.

1 Drawing Figure

1

The present invention relates to a new and distinct variety of hardy, dwarf, bush type rose plant of the miniature class; the variety being primarily characterized — as to novelty — by the white to near white buds and flowers which generally are of exhibition (Hybrid Tea) form.

The variety is further characterized by:

An abundance of bloom, with flowers usually borne singly, but also several to the stem in loose clusters.

Little or no fragrance.

A plant which is vigorous, of rounded, upright shape with small semi-glossy to matt foliage with pointed leaflets; the buds and flowers being similar in form and size to White Angel (miniature — U.S. Plant Pat. No. 3,538).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Little Darling (U.S. Plant Pat. No. 1,581, expired — floribunda) as the seed parent and Peachy White (miniature — not patented) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers. (Photo made of flowers grown in plastic greenhouse — color quite white).

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Mistee.

Flowers borne: Singly and several together (3 to 5) on slender wirey stems.

2

Quantity of bloom: Abundant both outside and in greenhouse.

Bud:

*Peduncle.*—Medium length; slender but sturdy; erect; medium to light green, sometimes tinted bronze (outdoors): with no prickles and numerous very short hairs.

*Before calyx breaks.*—Size — small. Form long; pointed with several foliaceous apendages and occasional hairs on surface of bud; with foliaceous parts extending beyond the tip of the bud equal to one-half or more of its length. Color — medium green, occasionally tinted with bronze (outdoors).

*As calyx breaks.*—Color — white. Opening: opens well in all weather.

Bloom: Size when fully open — small, averaging about 30 mm ($1\frac{1}{4}''$).

*Petalage.*—Double — averaging about 40 petals, arranged regularly plus several small petaloids.

*Form.*— Cupped or flat at first becoming more high centered with petals rolled loosely outward and downward. Open flowers may show stamens.

Petals: Fairly thick; satiny on inside and on outside surface.

*Shape.*—Outside petals, broad lanceolate (nearly round) with acute tip; intermediate — broad lanceolate with acute tip; inside — lanceolate with acute tip.

Color: Newly opened flower from a plant grown in plastic greenhouse (August 1979), Visalia, Calif.

*Outside petal.*—Outside surface — near white but tinted with soft yellow — near, but lighter than Primrose Yellow 601/3, becoming darker near base — near Primrose Yellow 601/2. Inside surface — lighter than Primrose Yellow 601/3 becoming more yellow toward base.

*Intermediate petal.*—Outside surface similar to outside petal. Inside surface similar to outside petal.

*Inner petal.*—Outside surface — same as intermediate petal; inside surface — same as intermediate petal. General color effect; buds and newly opened flowers — white; sometimes pale yellow (or cream) in center. Three days open — color (A) white when grown in greenhouse. (B) Outdoors — white, usually becoming tinted with soft pink along petal tips (similar to Garden Party — H. T. — U.S. Plant Pat. No. 1,814). Behavior — opens well in all weather. Spent petals drop off. Flower longevity (July — August 1979) — plant in pot 4–6 days or longer. Cut flowers at living room temperatures 3–5 days or longer.

Reproductive organs:

*Stamens.*—Arranged regularly about pistils.
*Filaments.*—Varying length, medium long, yellow.
*Anthers.*—Well formed; yellow.
*Pollen.*—Small amount.
*Pistils.*—Average number.
*Styles.*—Varying length; yellowish; bunched.
*Ovaries.*—All enclosed in calyx.
*Hips.*—None.
*Sepals.*—Permanent; spear shaped; recurved.
*Seed.*—None.

Foliage:

*Leaves.*—Compound of five (sometimes three or seven) leaflets; medium small; leathery; semi-glossy to matt.
*Leaflets.*—Shape: broad, nearly oval; apex acute; base rounded — sometimes acute. Color: medium green; new growth — normal (medium) green (sometimes tinted reddish, especially on back side of leaf). Rachis: medium strength; upper side may have several tiny short prickles or hairs; grooved; underside may have several thorns (1 to 3) and few to several tiny short prickles. Stipules: medium to short length; medium width; medium length narrow points which turn out usually at about 45 degrees or more.

Growth:

*Habit.*—Dwarf; bushy; rounded; much branched.
*Growth.*—Free vigorous; internodes short.
*Canes.*—Medium; slender; sturdy.
*Main stems.*—Color: medium green.
*Thorns.*—Few to none. Prickles — none. Hairs — none.
*Branches.*—Color: medium green. Thorns: few or none; slender. Prickles: none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by (A) buds and flowers of exhibition form, essentially white in color, the petals being lightly tinted with yellow in the opening stages (buds and flowers resembling White Angel — miniature — U.S. Plant Pat. No. 3,538 — in size, form and color) and (B) as grown outdoors — essentially same as above but petal tips being tinted with pink in a pattern resembling Garden Party (H. T., U.S. Plant Pat. No. 1,814, expired); and further characterized by a plant of compact well rounded shape, vigorous, with the main stems and shoots being nearly thornless, the said plant being easy to propagate from cuttings or by budding, with an abundance of small semi-glossy to matt foliage and an abundance of flowers borne singly or several to the stem in loose clusters.

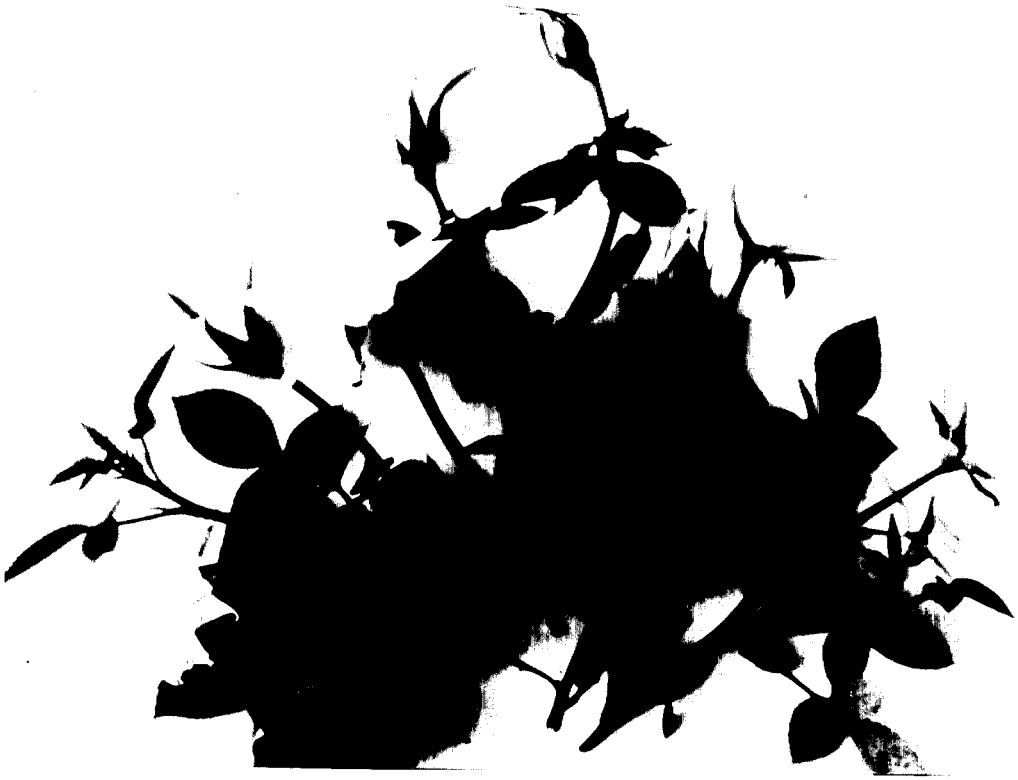

* * * * *